United States Patent
Nestler et al.

[11] Patent Number: 6,130,330
[45] Date of Patent: Oct. 10, 2000

[54] PROCESS FOR PREPARING MACROPOLYCYCLIC POLYAMINES

[75] Inventors: Bernd Nestler, Frankfurt; Michael Seebach, Hattersheim, both of Germany

[73] Assignee: Clariant GmbH, Frankfurt, Germany

[21] Appl. No.: 09/262,044

[22] Filed: Mar. 4, 1999

[30] Foreign Application Priority Data

Mar. 5, 1998 [DE] Germany ............... 198 09 543

[51] Int. Cl.[7] ............... C07D 487/22; C07D 257/02
[52] U.S. Cl. ............... 540/472; 540/477; 540/556; 544/338; 544/343
[58] Field of Search ............... 540/472, 477, 540/556; 544/338, 343

[56] References Cited

U.S. PATENT DOCUMENTS

| | | | |
|---|---|---|---|
| 5,880,281 | 3/1999 | Argese et al. | 540/474 |
| 5,886,174 | 3/1999 | Ripa et al. | 540/474 |

FOREIGN PATENT DOCUMENTS

| | | |
|---|---|---|
| 0427595 | 5/1991 | European Pat. Off. |
| WO 96/28432 | of 1996 | WIPO. |
| WO 97/05123 | 2/1997 | WIPO. |
| WO 97/08157 | 3/1997 | WIPO. |

OTHER PUBLICATIONS

"Synthesis and Transition–Metal Complexes of New Cross--Bridged Tetraamine Ligands" G. Weisman, E. Wong, D. Hill, M. Rogers, D. Reed, and J. Calabrese, Chem Commun 1996, pp. 947–948.

"Preparation and Stereochemistry of 1,4,8,11–Tetraazaperhydropyrene Derivatives From N,N'–BIS (3–Aminopropyl) Ethylenediamine" T. Okawara, H. Takaishi, Y. Okamoto, T. Yamasaki, and M. Furukawa, Heterocycles, vol. 41, No. 5, 1995, pp. 1023–1033.

Primary Examiner—Mukund J. Shah
Assistant Examiner—Pavanaram K Sripada
Attorney, Agent, or Firm—Miles B. Dearth; Scott E. Hanf

[57] ABSTRACT

What is claimed is a process for preparing macropolycyclic polyamines of the formula

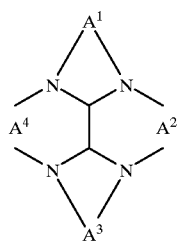

where $A^1$, $A^2$, $A^3$ and $A^4$ are as defined in the description. These compounds are prepared by a novel improved process by reacting a cyclic amine of the formula

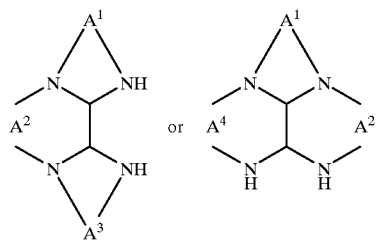

with a compound of the formula $X-A^2-Y$ or $X-A^3-Y$ where $A^1$, $A^2$, $A^3$ and $A^4$ are as defined in the description and X and Y are a leaving group.

6 Claims, No Drawings

PROCESS FOR PREPARING MACROPOLYCYCLIC POLYAMINES

FIELD OF THE INVENTION

This invention relates to a novel process for preparing specific macropolycyclic polyamines having a skeleton of the structure (1)

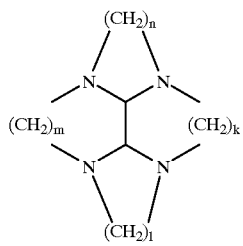

in which k, l, m and n independently of one another are numbers from 2 to 4 which may serve, for example, as starting materials for the preparation of other cyclic polyamine compounds. Such polyamine compounds can be used, for example, for synthesizing pharmacologically active substances, ligands for catalytically active metal complexes, host compounds for supramolecular structures or proton sponges.

It is problematic that the starting materials for the preparation of these macropolycyclic polyamines can only be prepared at great expense and in some cases with only low yields, since the methods which have hitherto been described have generally been worked out only for the synthesis of small amounts for scientific purposes.

This is illustrated using the synthesis of cis-perhydro-3a,5a,8a,10a-tetraazapyrene (2) (formula (1) where k, m=2 and l, n=3) as an example. The following processes are known to achieve this.

Reaction of cyclam (1,4,8,11-tetraazacyclotetradecane) (3) with glyoxal in acetonitrile was described by G. Weisman, E. Wong, D. Hill, M. Rogers, D. Reed and J. Calabrese in Chem. Commun. 1996, 947–948.

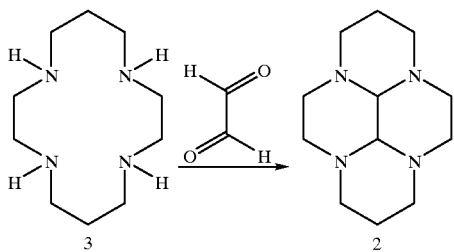

Here, cis-perhydro-3a,5a,8a,10a-tetraazapyrene is obtained in a yield of 80%. In addition to toxic acetonitrile being employed as solvent, especially the use of the macrocycle cyclam, which is difficult to obtain, as starting material is problematic. For preparing cyclam, the following processes have been described: WO 9708157 describes a three-step process in which initially 1,3-diaminopropane is cyclized with chloroacetyl chloride to give the bisamide 1. This is cyclized in the subsequent step with 1,3-diaminopropane in a highly dilute solution to give 2,10-dioxo-1,4,8,11-tetraazacyclotetradecane (II), and the latter is reduced to cyclam:

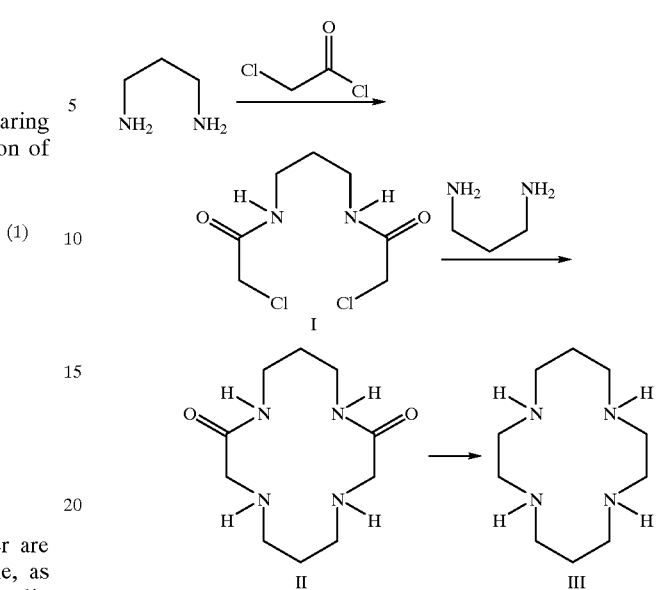

Here, the reducing agent used is Red-Al®, which is difficult to handle, not least for safety reasons; yields are not mentioned for any of the three reaction steps.

Another multistep process for preparing cyclam is described in WO 9705123. Here, 1,10-diamino-4,7-diazadecane is reacted with a 4-5-fold excess of toluenesulfonyl chloride to give III which is cyclized with ethylene glycol ditosylate, which is prepared in a separate step, to give the tetratosylate IV, which is finally detosylated.

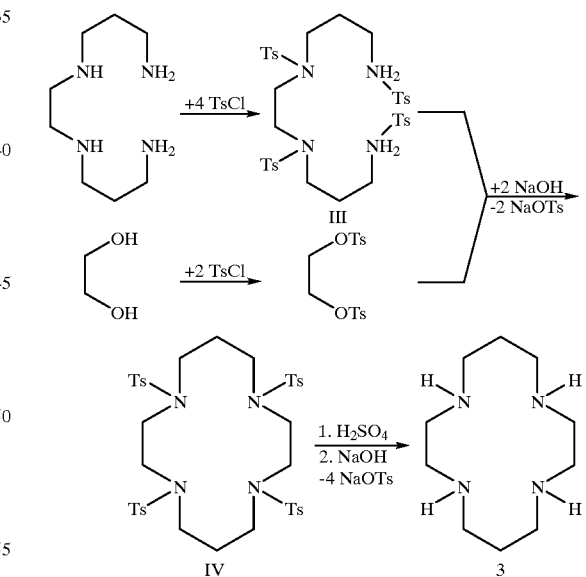

The disadvantages of this process are, in particular, the amounts of starting materials required, and the amounts of waste formed. Per mole of cyclam formed, six equivalents of toluenesulfonyl chloride are required, and 6 mol of toluenesulfonic acid in salt form are correspondingly produced as waste.

A further preparation process for cyclam is disclosed in EP 427595. Starting from 1,2-diaminoethane and acrylonitrile, 1,9-diamino-3,7-diazanonane is synthesized. Addition of nickel(II) chloride gives the corresponding nickel complex, which is converted with glyoxal into the bisimino derivative V, which is catalytically hydrogenated to the nickel-cyclam complex VI. Demetallation by addition of sodium cyanide gives cyclam in a yield of 60%.

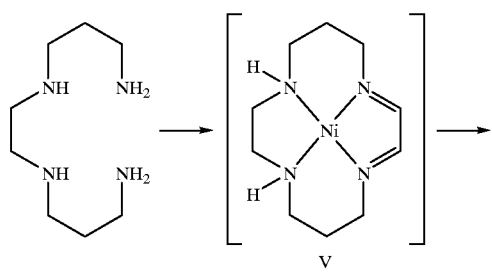

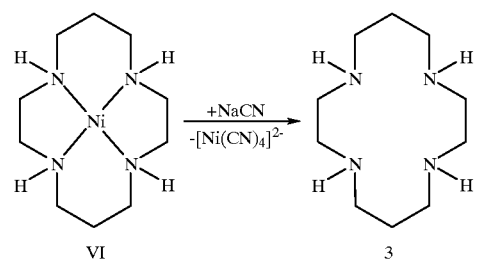

Critical in this template synthesis is, in addition to the use of allergenic nickel, in particular the highly toxic cyanide which is used for decomplexation, and the formation of cyanonickel compounds as waste products.

As a further route to perhydro-3a,5a,8a,10a-tetraazapyrene, T. Okawara, H. Takaishi, Y. Okamoto, T. Yamasaki, M. Furukawa mention, in Heterocycles 41 (1995) 1023–1033, the reduction of the dibenzotriazoylperhydrotetraazapyrene VII, obtained by successive reaction of 1,9-diamino-3,7-diazanonane with glyoxal and benzotriazole, with sodium borohydride; the tetrabenzotriazoylperhydrotetraazapyrene VIII resulting from 2,2-bis(hexahydropyrimidine) can be reduced correspondingly.

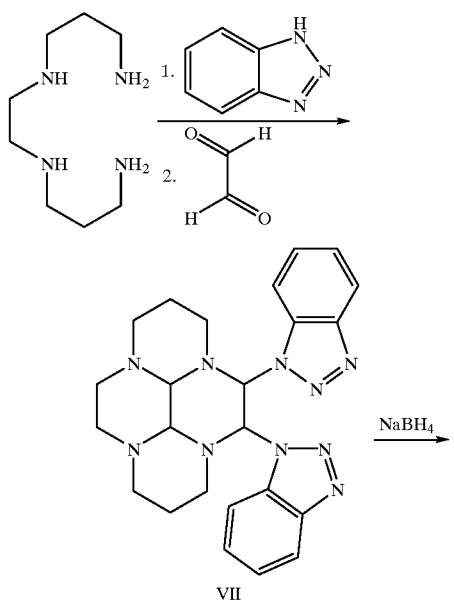

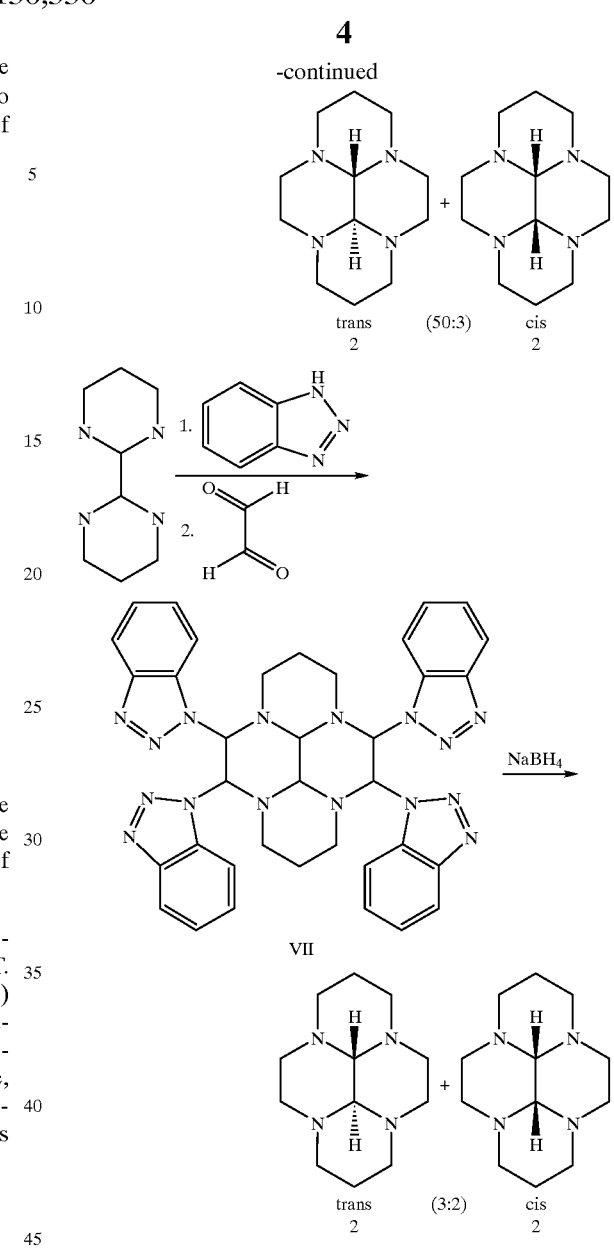

Here, in each case, diastereomer mixtures of trans- and cis-perhydro-3a,5a,8a,10a-tetraazapyrene are obtained, the trans-isomer dominating in each case. A disadvantage of this process is the use of benzotriazole, which is eliminated and obtained as waste.

These known processes for preparing the desired polycyclic compounds having a skeleton of the formula (1) are therefore unsuitable for preparing industrial amounts of these macrocycles, owing to in some cases complicated, multistep reaction protocols and reagents which are difficult to handle being employed.

SUMMARY OF THE INVENTION

It is the object of the present invention to provide a simple process for synthesizing polycyclic compounds having a skeleton of the formula (1). Furthermore, the process according to the invention shall be suitable for preparing industrial amounts, and the resulting products are to be obtained in high yield, with minimum amounts of waste.

The invention, accordingly, provides a process for preparing polycyclic compounds of the formula (4)

(4)

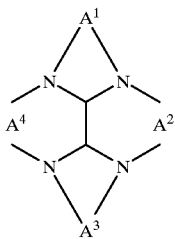

in which

A$^1$, A$^2$, A$^3$ and A$^4$ independently of one another are either a C$_2$- to C$_4$-alkylene radical which may be substituted by one or more groups P and/or Q where P is a C$_1$- to C$_{30}$-alkyl or cycloalkyl group which may be substituted by one or more groups Q, and Q is a group of the type
  -COR, in which R is a hydroxyl, a C$_1$- to C$_5$-alkoxy or C$_6$- to C$_{14}$-aryloxy or a substituted or unsubstituted amino group,
  a C$_6$- to C$_{14}$-aryl group which may be substituted by one or more C$_1$- to C$_{30}$-alkyl, cycloalkyl, aryl, C$_1$- to C$_5$-alkoxy, C$_6$- to C$_{14}$-aryloxy, substituted or unsubstituted amino groups, halogen atoms, cyano groups, sulfonyl groups, carboxyl groups or groups of the formula -(CH$_2$)$_r$-COOH, -(CH$_2$)$_r$-SO$_3$H, -(CH$_2$)$_r$-PO$_3$H$_2$, -(CH$_2$)$_r$ OH, where r is an integer from 0 to 4 and the abovementioned acid groups may also be present in salt form,
  an aromatic heterocycle which may contain nitrogen, oxygen and/or sulfur atoms and which may be substituted by one or more C$_1$- to C$_{30}$-alkyl, cycloalkyl, aryl, C$_1$- to C$_5$-alkoxy, C$_6$- to C$_{14}$-aryloxy, substituted or unsubstituted amino groups, halogen atoms, cyano groups, sulfonyl groups, carboxyl groups, or groups of the formula -(CH$_2$)$_r$-COOH, -(CH$_2$)$_r$-SO$_3$H, -(CH$_2$)$_r$-PO$_3$H$_2$, -(CH$_2$)$_r$ OH, where r is an integer from 0 to 4 and the abovementioned acid groups may also be present in salt form,
  a substituted or unsubstituted amino group,
  a hydroxyl group,
  a C$_1$- to C$_{30}$-alkyl or cycloalkyl group,
  a C$_1$- to C$_{30}$-alkoxy or C$_6$- to C$_{14}$-aryloxy group,
  a halogen atom,
  a cyano, sulfonyl or carboxyl group,
  a group of the formula -(CH$_2$)$_r$-COOH, -(CH$_2$)$_r$-SO$_3$H, -(CH$_2$)$_r$-PO$_3$H$_2$, -(CH$_2$)$_r$ OH, where r is an integer from 0 to 4 and the abovementioned acid groups may also be present in salt form; or A$^1$, A$^2$, A$^3$ and A$^4$ are a group -(CH$_2$)$_s$-E-(CH$_2$)$_t$-, in which E is a C$_6$- to C$_{14}$-arylene radical which may be substituted by groups P and/or Q, where the groups P and Q are as defined above and s and t independently of one another may have the values 0, 1 or 2.

DESCRIPTION OF THE PREFERRED EMBODIMENTS

Preference is given to preparing compounds of the abovementioned formula where A$^1$, A$^2$, A$^3$ and A$^4$ are a C$_2$-C$_4$-alkylene radical.

This process comprises reacting a cyclic amine of the formula 5A or 5B

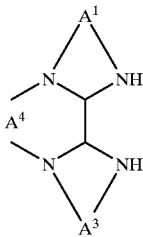

(5A)

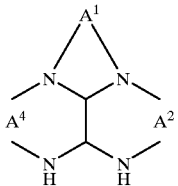

(5B)

with a compound of the formula

 (6A)

or

 (6B)

where A$^1$, A$^2$, A$^3$ and A$^4$ in the formulae 5 and 6 independently of one another are as defined above and X or Y independently of one another are a leaving group.

The cyclic amines of the formula 5A or 5B which serve as starting materials for the process according to the invention can be prepared by condensation of glyoxal with tetraamines, as described, for example, by R. Müller, W. von Philipsborn, L. Schleifer, P. Aped and B. Fuchs in Tetrahedron 47 (1981) 1013–1036. Examples of skeletons of such cyclic amines are cis- and trans-octahydro-2a,5,6,8a-tetraazaacenaphthylene (from 1,8-diamino-3,6-diazaoctane), cis- and trans-octahydro-1,3a,6a,9-tetraazaphenalene (from 1,9-diamino-3,7-diazanonane), cis- and trans-dodecahydro-4,5,8a,10a-tetraazaphenanthrene (from 1,10-diamino-4,7-diazadecane), cis- and trans-dodecahydro-1,4a,7a,11-tetraazadibenzo[ac]cycloheptene (from 1,11-diamino-4,8-diazaundecane).

The term leaving group refers to groups which are eliminated under the chosen reaction conditions from the compounds of the formula 6A or 6B during the preparation of the polyamines 4, without being replaced by other groups. These include, in particular, the p-toluene-, benzene- and methanesulfonic acid groups, and the halides chloride, bromide and iodide.

The reaction is usually carried out in the presence of a solvent. Here, preferred solvents are polar organic solvents, such as, for example, alcohols, glycols, ethers, ketones, esters, carboxamides, haloalkanes and sulfoxides, or mixtures of these. Particular preference is given to alcohols, glycols and carboxamides having short and intermediate alkyl or cycloalkyl radicals.

The solvents used can be employed without any further purification or drying. The yields drop noticeably only when the amount of water present in the solvent exceeds 3–5%.

The amount of solvent employed for the reaction is usually such that the compounds 5A or 5B and 6A and 6B are dissolved. If dissolution is incomplete, it is also possible to operate in dispersion (suspension or emulsion). The concentration of compounds of the formulae 5A or 5B and 6A or 6B is usually in the range of from 0.01 to 2.5 mol per liter of solvent, preferably from 0.05 to 1.2 mol/l, particularly preferably from 0.1 to 0.7 mol/l.

The reaction according to the invention can be carried out advantageously in the presence of one or more bases. Suitable bases are inorganic or organic bases. Examples of these which may be mentioned are: metal hydrides, metal amides, metal hydroxides, metal carbonates, metal bicarbonates, metal phosphates, metal hydrogen phosphates and/or organic amines. Preference is given to using alkali metal carbonates and amines. In general from 0.8 to 10.0 molar equivalents, preferably from 0.9 to 5.0 molar equivalents, particularly preferably from 1.0 to 2.5 molar equivalents of base are employed per equivalent of proton to be cleaved off of the secondary nitrogen atom of the compounds of the formula 5A or 5B. The base can be introduced in solid form or dissolved or suspended in the abovementioned solvents. Examples of solid bases are powders, flakes, microprills or pellets.

The reaction is carried out at temperatures between 10 and 200° C., preferably between 50 and 150° C. Depending on the chosen temperature, the period of time required for the reaction is approximately 1 hour to 8 days. Since an increase in the reaction temperature generally results in a reduction in the reaction time, it is advantageous to carry out the reaction at elevated temperature, if appropriate in the vicinity of the boiling point of the solvent.

To carry out the process according to the invention, in general a mixture of the compounds of the formulae 5A or 5B and 6A or 6B, the solvent and, if appropriate, the base is heated to the reaction temperature. Here, it is immaterial in which order the individual components of the reaction mixture are added.

After the reaction has ended, the target compound formed is, if required, isolated from the reaction mixture using customary methods. Suitable methods are, for example, filtration, extraction, distillative, chromatographic and osmotic methods, and combinations of these methods. To avoid side reactions, the reaction and, if appropriate, work-up are carried out under protective gas, usually nitrogen.

The process according to the invention is preferably employed for preparing polycyclic polyamines having a skeleton such as cis- and trans-decahydro-2a,4a,6a,8a-tetraazacyclopenta[fg]-acenaphthylene, cis- and trans-decahydro-2a,4a,7a,9a-tetraazacyclopenta[cd]phenalene, cis- and trans-decahydro-3a,5a,8a,10a-tetraazapyrene, cis- and trans-decahydro-3a,5a,8a,11a-tetraazacyclohepta[def]-phenanthrene or cis- and trans-decahydro-3a,6a,9a,12a-tetraazadibenzo[ef,kl]heptalene.

The process according to the invention is distinguished in particular by the following advantages:
low amounts of waste
very good yields
easily obtainable starting materials which are in some cases commercially available, even in great quantities
in some instances control of the isomer ratio of the product by selection of the reaction conditions.

The following examples, which are typical for the reaction protocol, serve to illustrate the process according to the invention in more detail and do not constitute a limitation of the applicability of the process.

Example 1

Synthesis of cis-octahydro-1,3a,6a,9-tetraazaphenalene

With cooling, a solution of 7.26 g of a 40% aqueous glyoxal solution was added dropwise over a period of 15 minutes to a solution of 8.01 g of 1,9-diamino-3,7-diazanonane in 30 ml of ethanol. The mixture was allowed to stand for one hour and then evaporated to dryness. This gave 18.2 g of a light-yellow solid.

Example 2

Synthesis of trans-dodecahydro-4,5,8a,10a-tetraaza-phenanthrene

A solution of 87.2 g of 1,10-diamino-4,7-diazadecane in 500 ml of toluene was admixed with 72.3 g of a 40% aqueous glyoxal solution, and the mixture was refluxed, with a water separator fitted, for 3 hours. When the solution was cooled, a solid precipitated out which was filtered off with suction, washed three times with 50 ml of toluene each time and dried under reduced pressure. This gave 34.9 g of pale yellow needles.

Example 3

Synthesis of cis-decahydro-3a,5a,8a,10a-tetraazapyrene

A mixture of 9.11 g of cis-octahydro-1,3a,6a,9-tetraazaphenalene, 19.2 g of 1,3-propanediol di-(p-toluenesulfonate), 6.91 g of potassium carbonate and 50 ml of dry ethanol was heated at the boil under reflux for 8 hours. The reaction mixture was filtered, the filtrate was evaporated to dryness and the product was extracted from the residue obtained in this manner using 50 ml of methylene chloride. Removal of the solvent on a rotary evaporator gave 8.22 g of a yellow-brown oil; vacuum distillation gave a colorless product.

Example 4

Synthesis of cis-decahydro-3a,5a,8a,10a-tetraazapyrene

Cis-decahydro-3a,5a,8a,10a-tetraazapyrene was synthesized as described in Example 3, but 1,3-dibromopropane instead of propanediol di-(p-toluenesulfonate) was converted in the reaction.

Example 5

Synthesis of trans-decahydro-3a,5a,8a,10a-tetraazapyrene

Trans-decahydro-3a,5a,8a,10a-tetraazapyrene was synthesized as described in Example 3, but triethylamine was employed instead of potassium carbonate.

Example 6

Synthesis of trans-decahydro-3a,5a,8a,10a-tetraazapyrene

Trans-decahydro-3a,5a,8a,10a-tetraazapyrene was synthesized as described in Example 3, but pyridine instead of potassium carbonate was employed in the reaction.

Example 7

Synthesis of trans-decahydro-3a,5a,8a,10a-tetrazapyrene

A mixture of 5.90 g of trans-dodecahydro-4,5,8a,10a-tetraazaphen-anthrene, 11.1 g of 1,2-ethanediol di-(p-toluenesulfonate), 4.20 g of potassium carbonate and 80 ml of dry N-methylpyrrolidone was heated at 130° C. for 2.5 hours and subsequently at 180° .C for 6 hours. The reaction mixture was evaporated to dryness and the product was extracted from the residue obtained in this manner using 50 ml of methylene chloride. Removal of the solvent on a rotary evaporator gave 6.52 g of a yellow-brown oil.

What is claimed is:

1. A process for preparing polycyclic compounds of the formula

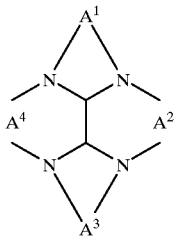

in which $A^1$, $A^2$, $A^3$ and $A^4$ independently of one another are either a $C_2$- to $C^4$-alkylene radical which is substituted by one or more groups P and/or Q where P is a $C_1$- to $C_{30}$-alkyl or cycloalkyl group which may be substituted by one or more groups Q, and Q is a group of the type -COR, in which R is a hydroxyl, a $C_1$- to $C_6$ -alkoxy or $C_6$- to $C_{14}$-aryloxy or a substituted or unsubstituted amino group, a $C_6$- to $C_{14}$-aryl group which may be substituted by one or more $C_1$- to $C_{30}$-alkyl, cycloalkyl, aryl, $C_1$- to $C_5$-alkoxy, $C_6$- to $C_{14}$ -aryloxy, substituted or unsubstituted amino groups, halogen atoms, cyano groups, sulfonyl groups, carboxyl groups or groups of the formula -$(CH_2)_r$-COOH, -$(CH_2)_r$-$SO_3H$, -$(CH_2)_r$-$PO_3H_2$, -$(CH_2)_r$ OH, where r is an integer from 0 to 4 and the abovementioned acid groups may also be present in salt form, an aromatic heterocycle which may contain nitrogen, oxygen and/or sulfur atoms and which may be substituted by one or more $C_1$- to $C_{30}$-alkyl, cycloalkyl, aryl, $C_1$- to $C_5$-alkoxy, $C_6$- to $C_{14}$ -aryloxy, substituted or unsubstituted amino groups, halogen atoms, cyano groups, sulfonyl groups, carboxyl groups, or groups of the formula -$(CH_2)_r$-COOH, -$(CH_2)_r$-$SO_3H$, -$(CH_2)_r$-$PO_3H_2$, -$(CH_2)_r$OH, where r is an integer from 0 to 4 and the abovementioned acid groups may also be present in salt form, a substituted or unsubstituted amino group, a hydroxyl group, a $C_1$- to $C_{30}$-alkyl or cycloalkyl group, a $C_1$- to $C_{30}$-alkoxy or $C_6$- to $C_{14}$-aryloxy group, a halogen atom, a cyano, sulfonyl or carboxyl group, a group of the formula -$(CH_2)_r$-COOH, -$(CH_2)_r$-$SO_3H$, -$(CH_2)_r$-$PO_3H_2$, -$(CH_2)_r$ OH, where r is an integer from 0 to 4 and the abovementioned acid groups may also be present in salt form;

or $A^1$, $A^2$, $A^3$ and $A^4$ are a group -$(CH_2)_s$-E-$(CH_2)_t$-, in which E is a $C_6$- to $C_{14}$-arylene radical which may be substituted by groups P and/or Q, where the groups P and Q are as defined above and s and t independently of one another may have the values 0, 1 or 2, which comprises reacting a cyclic amine of the formula

(5A)

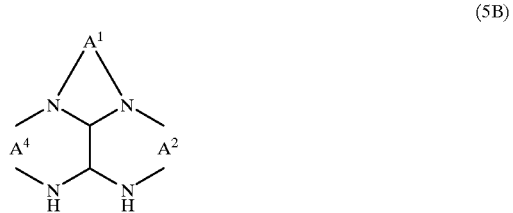

(5B)

with a compound of the formula

X—$A^2$—Y  (6A)

or

X—$A^3$—Y  (6B)

where $A^1$, $A^2$, $A^3$ and $A^4$ independently of one another are as defined above and X or Y independently of one another are a leaving group.

2. The process as claimed in claim 1, wherein compounds of said formula are prepared where $A^1$, $A^2$, $A^3$ and $A^4$ independently of one another are a $C_2$-$C_4$-alkylene radical.

3. The process as claimed in claim 1, wherein the reaction is carried out in the presence of a polar organic solvent.

4. The process as claimed in claim 1, wherein the reaction is carried out in the presence of a base.

5. The process as claimed in claim 1, wherein the reaction is carried out at temperatures from 10 to 200° C.

6. A process for preparing polycyclic compounds of the formula

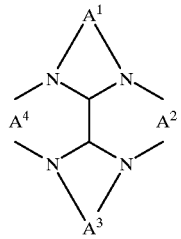

in which $A^1$, $A^2$, $A^3$ and $A^4$ independently of one another are -$(CH_2)_s$-E-$(CH_2)_t$-, in which E is a $C_6$- to $C_{14}$-arylene radical, where s and t independently of one another may have the values 0, 1 or 2 and $A^1$, $A^2$, $A^3$ and $A^4$ may be substituted by one or more groups P and/or Q where P is a $C_1$- to $C_{30}$-alkyl or cycloalkyl group which may be substituted by one or more groups Q, and Q is a group of the type
- -COR, in which R is a hydroxyl, a $C_1$- to $C_5$-alkoxy or $C_6$- to $C_{14}$-aryloxy or a substituted or unsubstituted amino group,
- a $C_6$- to $C_{14}$-aryl group which may be substituted by one or more $C_1$- to $C_{30}$-alkyl, cycloalkyl, aryl, $C_1$- to $C_5$-alkoxy, $C_6$- to $C_{14}$-aryloxy, substituted or unsubstituted amino groups, halogen atoms, cyano groups, sulfonyl groups, carboxyl groups or groups of the formula -$(CH_2)_r$-COOH, -$(CH_2)_r$-$SO_3H$, -$(CH_2)_r$-$PO_3H_2$, -$(CH_2)_r$ OH, where r is an integer from 0 to 4 and the abovementioned acid groups may also be present in salt form,
- an aromatic heterocycle which may contain nitrogen, oxygen and/or sulfur atoms and which may be substituted by one or more $C_1$- to $C_{30}$-alkyl, cycloalkyl, aryl, $C_1$- to $C_5$-alkoxy, $C_6$- to $C_{14}$-aryloxy, substituted or unsubstituted amino groups, halogen atoms, cyano groups, sulfonyl groups, carboxyl groups, or groups of the formula -$(CH_2)_r$-COOH, -$(CH_2)_r$-$SO_3H$, -$(CH_2)_r$-$PO_3H_2$, -$(CH_2)_r$ OH, where r is an integer from 0 to 4 and the abovementioned acid groups may also be present in salt form,
- a substituted or unsubstituted amino group,
- a hydroxyl group,
- a $C_1$- to $C_{30}$-alkyl or cycloalkyl group,
- a $C_1$- to $C_{30}$alkoxy or $C_6$- to $C_{14}$-aryloxy group,
- a halogen atom,
- a cyano, sulfonyl or carboxyl group,
- a group of the formula -$(CH_2)_r$-COOH, -$(CH_2)_r$-$SO_3H$, -$(CH_2)_r$-$PO_3H_2$, -$(CH_2)_r$ OH, where r is an integer from 0 to 4 and the abovementioned acid groups may also be present in salt form;

which comprises reacting a cyclic amine of the formula

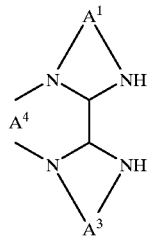 (5A)

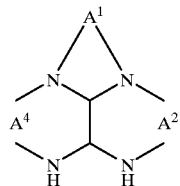 (5B)

with a compound of the formula

 (6A)

or

 (6B)

where $A^1$, $A^2$, $A^3$ and $A^4$ independently of one another are as defined above and X or Y independently of one another are a leaving group.

* * * * *